United States Patent [19]
Farina et al.

[11] Patent Number: 5,985,905
[45] Date of Patent: Nov. 16, 1999

[54] INDOLE DERIVATIVES FOR THE TREATMENT OF OSTEOPOROSIS

[76] Inventors: Carlo Farina; Guy Marguerite Marie Gérard Nadler; Pierfausto Seneci, all of SmithKline Beecham Corporation, Corporate Intellectual Property - UW2220, P.O. Box 1539, King of Prussia, Pa. 19406-0939

[21] Appl. No.: 09/214,648

[22] PCT Filed: Jul. 7, 1997

[86] PCT No.: PCT/EP97/03711

§ 371 Date: May 5, 1999

§ 102(e) Date: May 5, 1999

[87] PCT Pub. No.: WO98/01445

PCT Pub. Date: Jan. 15, 1998

[30] Foreign Application Priority Data

Jul. 9, 1996 [GB] United Kingdom .................. 9614402

[51] Int. Cl.$^6$ ...... A61K 31/405; A61K 31/425; C07D 403/06; C07D 417/06
[52] U.S. Cl. .......... 514/369; 514/414; 548/183; 548/468
[58] Field of Search .................. 548/468, 183; 514/414, 369

[56] References Cited

U.S. PATENT DOCUMENTS 5,296,499 3/1994 Sohda et al. ............................ 514/419

FOREIGN PATENT DOCUMENTS 1274048 5/1972 United Kingdom ............ C09B 23/00

*Primary Examiner*—Joseph K. McKane

[57] ABSTRACT

The invention relates to indole compounds, a process for preparing, pharmaceutical compositions containing the compounds and treating diseases associated with over activity of osteoclasts.

8 Claims, No Drawings

INDOLE DERIVATIVES FOR THE TREATMENT OF OSTEOPOROSIS

This invention relates to certain novel compounds, to a process for preparing such compounds, to pharmaceutical compositions containing such compounds and to the use of such compounds and compositions in medicine.

Co-pending International Application, application number PCT/EP96/00157 discloses certain indole derivatives which are indicated to reduce bone resorption by inhibiting osteoclast H$^+$-ATPase.

Diseases associated with loss of bone mass are known to be caused by over activity of osteoclast cells. It is also known that certain compounds, usually related to bafilomycin, are useful for treating such diseases: For example International Patent Application, publication number WO 91/06296 discloses certain bafilomycin macrolides for the treatment of bone affecting diseases.

However, bafilomycin derivatives are not selective for osteoclasts in humans. The use of these compounds is therefore associated with unacceptable toxicity due to generalised blockade of other essential v-ATPases. Indeed, to date there is no known treatment which is selective for the human osteoclasts.

The search for a successful treatment for diseases associated with loss of bone mass in humans is further complicated in that the nature of the therapeutic target for the selective inhibition of the osteoclasts is controversial. Thus Baron et al (International Patent Application publication number WO93/01280) indicate that a specific vacuolar ATPase (V-ATPase) has been identified in osteoclasts as a potential therapeutic target. However, the Baron work was carried out in chickens and Hall et al (Bone and Mineral 27, 1994, 159–166), in a study relating to mammals, conclude that in contrast to avian osteoclast V-ATPase, mammalian osteoclast V-ATPase is pharmacologically similar to the v-ATPase in other cells and, therefore, it is unlikely to be a good therapeutic target.

We have now found a group of compounds which are selective for mammalian osteoclasts, acting to selectively inhibit their bone resorbing activity. These compounds are therefore considered to be particularly useful for the treatment and/or prophylaxis of diseases associated with loss of bone mass, such as osteoporosis and related osteopenic diseases, Paget's disease, hyperparathyroidism and related diseases. These compounds are also considered to possess anti-tumour activity, antiviral activity (for example against Semliki Forest, Vesicular Stomatitis, Newcastle Disease, Influenza A and B, HIV viruses), antiulcer activity (for example the compounds may be useful for the treatment of chronic gastritis and peptic ulcer induced by *Helicobacter pylori*), immunosupressant activity, antilipidemic activity, antiatherosclerotic activity and to be useful for the treatment of AIDS and Alzheimer's disease. In a further aspect, these compounds are also considered useful in inhibiting angiogenesis, i.e. the formation of new blood vessels which is observed in various types of pathological conditions (angiogenic diseases) such as rheumatoid arthritis, diabetic retinopathy, psoriasis and solid tumours.

Accordingly, the present invention provides a compound of formula (I):

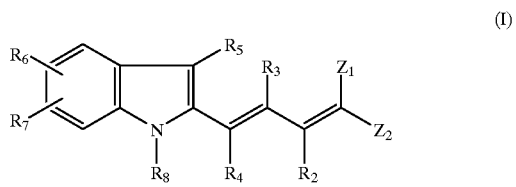

or a salt thereof, or a solvate thereof, wherein:
$R_2$, $R_3$ and $R_4$ each independently represent hydrogen, alkyl, aryl or substituted aryl;
$R_5$ represents hydrogen, alkyl, aryl or substituted aryl;
$R_6$ and $R_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino;
$R_8$ represents hydrogen, hydroxy, alkanoyl, alkyl, aminoalkyl, hydroxyalkyl, carboxyalkyl, carbalkoxyalkyl, carbamoyl or aminosulphonyl; and
$Z_1$ and $Z_2$ together with the carbon atom to which they are attached represent a heterocyclic group.

Suitably, $Z_1$ and $Z_2$ together with the carbon atom to which they are attached represent a moiety of formula (a):

wherein the asterisked (*) carbon is attached to the double bond, $R_1$ represents hydrogen or a thioxo group; X represents O or $NR_9$ wherein $R_9$ is $C_{1-6}$ alkyl or an optionally substituted heterocyclic group or a group —T—$NR_sR_t$ wherein T is a $C_{1-6}$ alkylene group and $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together form a heterocyclic group; and Y represents $CH_2$, —$NR_{10}CH_2$— wherein $R_{10}$ is hydrogen or a $C_{1-6}$ alkyl group, or Y is —$OCH_2$— or S.

Suitably, $R_2$, $R_3$ and $R_4$ each independently represent hydrogen, alkyl or phenyl.
An example of $R_2$ is hydrogen.
An example of $R_3$ is hydrogen.
An example of $R_4$ is hydrogen.
Suitably, $R_5$ is hydrogen, alkyl or phenyl.
An example of $R_5$ is hydrogen.
When $R_6$ or $R_7$ represents alkoxy, said alkoxy group is suitably a $C_{1-6}$ alkoxy for example methoxy.
When $R_6$ or $R_7$ represents halo, said halo group is suitably a fluoro or chloro group.
When $R_6$ or $R_7$ represents alkyl, said alkyl group is suitably a $C_{1-6}$ alkyl for a example butyl group.
Suitable positions for substitution for $R_6$ or $R_7$ are the 4, 5, 6 or 7 position, favourably the 5 or 6 position.
A favoured value for $R_6$ is halo.
A favoured value for $R_7$ is halo.

In a preferred aspect $R_6$ is halo, especially 5-halo, and $R_7$ is halo, especially 6-halo.

An example of $R_8$ is hydrogen.

In one aspect X represents O.

In one aspect X represents $NR_9$.

Suitably, when X is $NR_9$, $R_9$ represents $C_{1-6}$ alkyl, for example methyl.

When $R_9$ is a heterocyclic group it is preferably attached at a carbon atom of said heterocyclic group.

Suitable heterocyclic groups represented by $R_9$ include optionally substituted piperidine groups wherein optional substituents are $C_{1-6}$ alkyl groups, especially methyl groups, for example a 2,2,6,6 tetramethylpiperidin-4-yl group.

When X represents $TNR_sR_t$, $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group.

When $R_s$ or $R_t$ represent substituted alkyl, favoured groups are 2-(dialkylamino)ethyl or 3-(dialkylamino)propyl or 4-(dialkylamino)butyl or heterocyclylmethyl or heterocyclylethyl or heterocyclylpropyl groups.

When $R_s$ or $R_t$ represent alkenyl or substituted alkenyl, suitable alkenyl groups are $C_{2-6}$ alkenyl groups, for example a $C_5$ alkenyl group.

When $R_s$ or $R_t$ represent aryl or substituted aryl, suitable aryl groups are phenyl groups.

Examples of the moiety of formula (a) include 1,4-dioxan-2-one, 1-methyl-2-pyrrolidone and 3-methyl-2-thioxothiazolidin-4-one.

As used herein, the term "alkyl" includes straight or branched chain alkyl groups having from 1 to 12, suitably 1 to 6, preferably 1 to 4, carbon atoms, such as methyl, ethyl, n- and iso-propyl and n-iso-, tert-butyl and pentyl groups, and also includes such alkyl groups when forming part of other groups such as alkoxy or alkanoyl groups.

Suitable optional substituents for any alkyl group include hydroxy; alkoxy; a group of formula $NR_uR_v$ wherein $R_u$ and $R_v$ each independently represent hydrogen, optionally substituted alkyl, optionally substituted cycloalkyl, optionally substituted aryl, optionally substituted arylalkyl, optionally substituted heterocyclyl, optionally substituted heterocyclylalkyl, carboxy, carboxyalkyl, or alkoxycarbonyl, nitro, or $R_u$ and $R_v$ together form an optionally substituted heterocyclic ring; carboxy; alkoxycarbonyl; alkoxycarbonylalkyl; alkylcarbonyloxy; alkylcarbonyl; mono- and di-alkylphosphonate; optionally substituted aryl; and optionally substituted heterocyclyl.

As used herein, the term "alkenyl" includes straight or branched chain alkenyl groups having from 2 to 12, suitably 2 to 6 carbon and also includes such groups when forming part of other groups, an example is a butenyl group, such as a 2-butenyl group.

Suitable optional substituents for any alkenyl group includes the alkyl substituents mentioned above.

As used herein, the term "aryl" includes phenyl and naphthyl, especially phenyl.

Suitable optional substituents for any aryl group include up to 5 substituents, suitably up to 3 substituents, selected from alkyl, substituted alkyl, alkoxy, hydroxy, halogen, trifluoromethyl, acetyl, cyano, nitro, amino, mono-and di-alkylamino and alkylcarbonylamino.

Preferred optional substituents for any aryl group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy)hydroxymethyl, Suitable arylalkyl groups include aryl-$C_{1-3}$-alkyl groups such as phenylethyl and benzyl groups, especially benzyl.

Preferably, substituted aralkyl groups are substituted in the aryl moiety.

As used herein, the terms "heterocyclyl" or "heterocyclic" include saturated or unsaturated single or fused, including spiro, ring heterocyclic groups, each ring having 4 to 11 ring atoms, especially 5 to 8, preferably 5, 6 or 7 which ring atoms include 1, 2 or 3 heteroatoms selected from O, S, or N.

Suitable heterocyclic groups include single ring saturated heterocyclic groups, single ring unsaturated heterocyclic groups, fused ring heterocyclic groups.

Fused ring heterocyclic groups include spiro heterocyclic groups.

Suitable single ring unsaturated heterocyclic groups comprise 5-, 6- or 7-membered rings.

Suitable 5-membered single ring unsaturated heterocyclic groups are furanyl, thienyl, pyrrolyl, pyrazolyl, imidazolyl, triazolyl, tetrazolyl, oxazolyl, isoxazolyl, furazanyl, thiazolyl and isothiazolyl groups; or partially saturated derivatives thereof, such as 4,5-dihydro-1,3-thiazol-2-yl, 1H-imidazolinyl, pyrrolinyl, pyrazolinyl, oxazolinyl, isoxazolinyl, thiazolinyl groups.

Suitable 6-membered single ring unsaturated heterocyclic groups are pyridyl, pyrimidinyl, pyridazinyl, pyrazinyl, triazinyl, tetrazinyl, 1,2- or 1,3- or 1,4-oxazinyl, 1,2- or 1,3- or 1,4-thiazinyl and pyranyl groups, or partially saturated derivatives thereof such as 1,2- or 1,3- or 1,4-dihydrooxazinyl, 1,4-dihydropyridyl, dihydropyridazinyl, dihydropyrazinyl or dihydropyrimidinyl.

Suitable 7-membered single ring unsaturated heterocyclic groups are azepinyl, oxepinyl, diazepinyl, thiazepinyl, oxazepinyl or partially saturated derivatives thereof.

Suitable, single ring saturated heterocyclic groups comprise 5-, 6- or 7-membered rings.

Suitable 5-membered single ring saturated heterocyclic groups are pyrrolidinyl, imidazolidinyl, pyrazolidinyl, oxazolidinyl, isoxazolidinyl and terahydrofuranyl groups.

Suitable 6-membered single ring saturated heterocyclic groups are piperidinyl, piperazinyl, tetrahydropyranyl, 1,3-dioxacyclohexyl, tetrahydro-1,4-thiazinyl, morpholinyl and morpholino groups.

Suitable 7-membered single ring saturated heterocyclic groups are hexamethyleniminyl, oxepanyl and thiepanyl.

Suitable fused ring heterocyclic groups include fused saturated rings, fused unsaturated rings and saturated rings fused to unsaturated rings.

Suitable groups having fused saturated rings are quinuclidyl, 8-azabicyclo[3.2.1]octyl, 9-azabicyclo[3.3.1]nonyl, 1-azabicyclo[3.3.3]undecyl, 1,9-diazabicyclo[3.3.1]nonyl and 1,5-diazabicyclo[3.3.1]nonyl groups.

Suitable groups having fused unsaturated rings are pyrazo[3.4-d]pyrimidinyl, 1,2,5-thiadiazolo[3,4-b]pyridyl, isoxazolo[4,5-b]pyridyl, thiazolo[4,5-b]pyridyl, oxazolo[4,5-d]pyrimidinyl, 7H-purin-2-yl, quinolyl, isoquinolyl, benzo[b]thienyl, benzofuranyl, isobenzofuranyl, benzoxazolyl, benzothiazolyl, indolizinyl, indolyl, isoindolyl, indazolyl, phthalazinyl, naphthyridinyl, quinoxalinyl, quinazolinyl, cinnolinyl, pteridinyl and β-carbolinyl groups.

Suitable groups having saturated rings fused to unsaturated rings includes groups which are fused to benzene rings such as tetrahydroquinolyl, 4H-quinolizinyl, tetrahydroisoquinolyl, dihydrobenzofuryl, chromenyl, chromanyl, isochromanyl, indolinyl and isoindolinyl groups.

Suitable spiro heterocyclic groups include oxaspiro[4.5] decyl, azaspiro[4.5]decyl, 1,2,4-triazaspiro[5.5]undecyl, 1,4-dioxa-9-azaspiro[4.7]dodecyl and 1-azaspiro[5.5] undecyl.

Suitable optional substituents for any heterocyclyl or heterocyclic group include up to 5 substituents, suitably up to 3 substituents, selected from alkyl, substituted alkyl, alkoxy, hydroxy, halo, amino, mono- or di-alkyl amino, alkoxycarbonyl, hydroxyalkyl, alkoxyalkyl, hydroxyalkoxyalkyl, alkoxyalkyloxyalkyl, aryl, aryloxy and heterocyclyl.

Preferred optional substituents for any heterocyclyl or heterocyclic group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy) hydroxymethyl.

For the avoidance of doubt a reference herein to "heterocylic" includes a reference to "heterocyclyl".

As used herein, the term "halo" includes fluoro, chloro and bromo, suitably fluoro and chloro, favourably chloro.

Certain of the carbon atoms of the compounds of formula (I)—such as those compounds wherein $R_1$–$R_8$ contains chiral alkyl chains are chiral carbon atoms and may therefore provide stereoisomers of the compound of formula (I). The invention extends to all stereoisomeric forms of the compounds of formula (I) including enantiomers and mixtures thereof, including racemates. The different stereoisomeric forms may be separated or resolved one from the other by conventional methods or any given isomer may be obtained by conventional stereospecific or asymmetric syntheses.

The compounds of formula (I) also possess two double bonds and hence can exist in one or more geometric isomers. The invention extends to all such isometric forms of the compounds of formula (I) including mixtures thereof. The different isomeric forms may be separated one from the other by conventional methods or any given isomer may be obtained by conventional synthetic methods. Suitable salts of the compounds of the formula (I) are pharmaceutically acceptable salts.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid or acetylsalicylic acid.

Suitable pharmaceutically acceptable salts of carboxy groups include metal salts, such as for example aluminium, alkali metal salts such as sodium or potassium and lithium, alkaline earth metal salts such as calcium or magnesium and ammonium or substituted ammonium salts, for example those with $C_{1-6}$ alkylamines such as triethylamine, hydroxy-$C_{1-6}$ alkylamines such as 2-hydroxyethylamine, bis-(2-hydroxyethyl)-amine or tri-(2-hydroxyethyl)-amine, cycloalkylamines such as dicyclohexylamine, or with procaine, 1,4-dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) or a salt thereof or a solvate thereof, may be prepared by reacting a compound of formula (II):

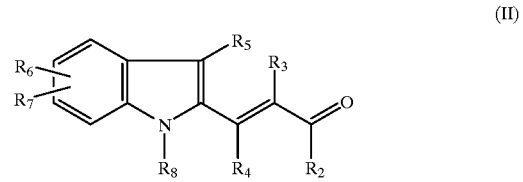

(II)

wherein $R_2$, $R_3$, $R_4$, $R_5$, $R_6$, $R_7$ and $R_8$ are as defined in relation to formula (I), with a reagent capable of converting the moiety of formula —$COR_2$ into a moiety of formula (b):

(b)

wherein $Z_1$ and $Z_2$ are as defined in relation to formula (I); and thereafter, as required carrying out one or more of the following reactions:

(i) converting one compound of formula (I) into another compound of formula (I);

(ii) removing any protecting group;

(iii) preparing a salt or a solvate of the compound so formed.

A suitable moiety (b) is a moiety of the above defined formula (a).

When moiety (b) is a moiety of the above defined formula (a), a suitable reagent capable of converting —$COR_2$ into said moiety (a), is a compound of formula (IIIA):

(IIIA)

wherein X and Y are as defined in relation to formula (I) and W represents O, S or $NR_x$ wherein $R_x$ is H, $C_{1-6}$ alkyl or $C_{1-6}$ alkylcarbonyl.

For compounds of formula (I) in which moiety (b) is a moiety (a) and wherein the moiety —X—C($R_1$)—Y— is —O($CH_2$)$_2$—O—, —O($CH_2$)$_2$—$NR_{10}$ or $R_9$N—($CH_2$)$_2$—$NR_{10}$, a suitable reagent is a compound of formula (IIIB)

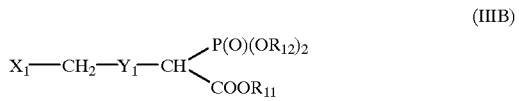

(IIIB)

wherein $X_1$ is O or $NR_9$ or a protected form thereof, $Y_1$ is —$CH_2$—O— or —$CH_2$N($R_{10}$)— and $R_{11}$ and $R_{12}$ each independently represent $C_{1-6}$ alkyl, suitably ethyl.

For compounds of formula (I) wherein the moiety of formula (b) is a (2-pyrrolidone)-5-ene group, a suitable reagent is a reagent of formula (IIIC):

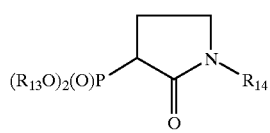

(IIIC)

wherein $R_{13}$ is $C_{1-6}$ alkyl while $R_{14}$ is $R_9$ or a group which can be transformed into $R_9$.

When the reagent is a compound of formula (IIIA) the reaction is carried out under conventional Knoevenagel conditions, for example using a solvent such as glacial acetic acid at any temperature providing a suitable rate of formation of the required product, usually at an elevated temperature and conveniently at the reflux temperatures of the solvent; suitably the reaction is carried out in the presence of an alkali metal acetate, for example sodium acetate; preferably the reaction is carried out in an inert atmosphere such as argon.

The reaction between the compounds of formula (II) and the reagent capable of converting the group of formula —$CO.R_2$ into the moiety of formula (b), may be carried out under the appropriate conventional conditions, depending upon the particular reagent chosen, for example when the required moiety (b) is a moiety of the above defined formula (a), and the reagent is a compound of formula (IIIB) the reaction is carried out under conventional Horner-Emmons conditions, using any suitable, aprotic solvent for example an aromatic hydrocarbon such as benzene, preferably, toluene or xylene, DMF, DMSO, chloroform, dioxane, dichloromethane, THF, acetonitrile, N-methylpyrrolidone and the like or mixtures thereof, preferably an anhydrous solvent, at a temperature providing a suitable rate of formation of the required product, conveniently at ambient temperature or at an elevated temperature, such as a temperature in the range of from 30° C. to 120° C.; preferably the reaction is conducted in the presence of a base.

Suitable bases for use in the last above mentioned reaction include organic bases, such as tetramethylguanidine (TMG), butyllithium, lithiumdiisopropylamide (LDA), N,N-diisopropylethylamine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as sodium hydride; and optionally the reaction is carried out in an inert atmosphere such as nitrogen.

Alternatively, when the reagent is a compound of formula (IIIB), then the reaction is carried out under conventional Wittig conditions. Usually, the reaction is carried out in the presence of a base, in any suitable aprotic solvent. Suitable bases are organic bases such as triethylamine, trimethylamine, N,N-diisopropylethylamine (DIPEA), pyridine, N,N-dimethylaniline, N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO) and inorganic bases such as sodium hydride, caesium carbonate, potassium carbonate, preferably sodium hydride. Suitable solvents are conventional solvents for use in this type of reaction, such as aromatic hydrocarbons such as benzene, toluene or xylene or the like; DMF, DMSO, chloroform, dioxane, dichloromethane, THF, ethyl acetate, acetonitrile, N-methylpyrrolidone or mixtures thereof, preferably dichloromethane. This reaction is carried out at any temperature providing a suitable rate of formation of the required product, conveniently at ambient temperature or at an elevated temperature, such as a temperature in the range of from −20° C. to 140° C., preferably in the range of from about room temperature to the reflux temperature of the solvent.

The reaction between the compounds of formula (II) and the reagent of formula (IIIB) proceeds via an intermediate which cyclises to provide the required 6-membered ring. When $X^1$ is a protecting group to the protecting group must be removed to allow cyclisation to the compound of formula (I). Suitable protecting groups are conventional groups described herein.

When the reagent is a compound of formula (IIIC), then the reaction is carried out in a solvent such as ethanol usually at an elevated temperature, such as a temperature in the range of 40° C. to 90° C. for example 60° C.; generally the reaction is carried out in the presence of a base, usually an organic base such as those mentioned above, for example triethylamine.

A compound of formula (II) may be prepared according to the reaction sequence shown in Scheme (I) below

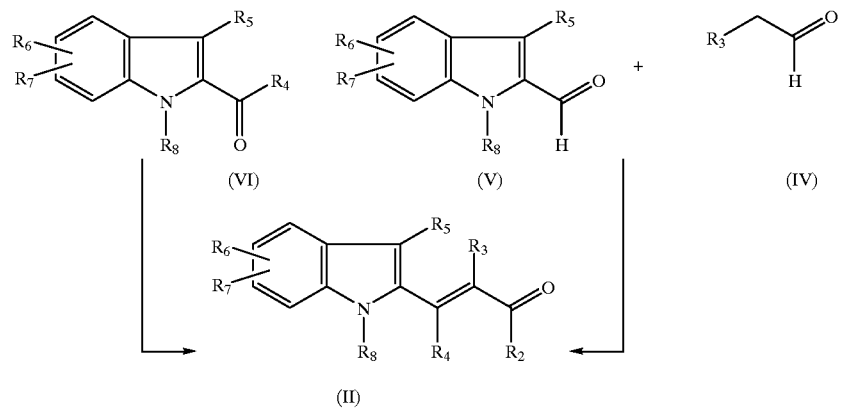

wherein, subject to any qualification mentioned below $R_2$, $R_3$, $R_4$, $R_5$, $R_6$, $R_7$ and $R_8$ are as defined in relation to the compounds of formula (I).

The reactions in Scheme (I) may be carried out using the appropriate conventional procedure, for example: when $R_2$ and $R_4$=H, aldehyde (V) can react with aliphatic aldehydes of formula (IV) in polar protic solvents such as methanol and ethanol and in the presence of a base such as sodium or potassium hydroxide affording compound (II).

Alternatively, compounds of formula (II) may be prepared by the Wittig reaction of keto derivatives of formula (VI) with an appropriate phosphonium salt or by Horner Emmons reaction of keto derivative (VI) with an appropriate phosphonate. Respective reaction conditions are the appropriate conventional conditions, for example for the Wittig reaction those described in "The Wittig Reaction", R. Adams Ed., Vol. 14, p. 270 (1965) or in Angew. Chem. Int. Ed. Engl., 4, 645 (1965) and for the Horner Emmons reaction those reported, in Tetrahedron Lett. 1981, 461; Can. J. Chem., 55, 562 (1997); J.Am.Chem.Soc., 102, 1390 (1980); J. Org. Chem., 44, 719 (1979); Syntheses, 1982, 391; and Tetrahedron Lett. 1982, 2183.

An appropriate phosphonium salt is a compound of formula (VIIA):

(VIIA)

wherein $R_3$ is as defined in relation to formula (I) and $R_u$ is $R_2$ as defined in relation to formula (I) (other than hydrogen) or a moiety $OR_v$ wherein $R_v$ is $C_{1-6}$ alkyl, such as ethyl. Hal$^-$ is a halogen anion, such as chloride or bromide.

An appropriate phosphonate is a compound of formula (VIIB):

(VIIB)

wherein $R_3$ and $R_u$ are as defined in relation to formula (VIIA) and $W_w$ is $C_{1-6}$ alkyl, such as ethyl.

The reactions of compounds of formula (VI) with the above mentioned phosphonium salts of formula (VIIA), wherein $R_u$ is $R_2$ (other than hydrogen) and the phosphonates of formula (VIIB), wherein $R_u$ is $R_2$ (other than hydrogen), are carried out using conventional Wittig or Horner Emmons conditions: solvents include aromatic hydrocarbons, such as benzene, toluene or xylene or the like; DMF, DMSO, chloroform, dioxane, dichloromethane, THF, ethyl acetate, acetonitrile, N-methylpyrrolidone and the like or mixtures thereof, in the presence of a base in any suitable solvent; suitable bases include organic bases, such as triethylamine, trimethylamine, N,N-diisopropylethylamine (DIPEA), pyridine, N,N-dimethylaniline, N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO) and inorganic bases, such as sodium hydride, caesium carbonate, potassium carbonate. Preferably, the reaction is carried out at a reaction temperature of in the range of about −20° C. to 140° C., preferably about room temperature to the reflux temperature of the solvent.

Alternatively, the reaction of the compound of formula (VI) with phosphonium salt (VIIA) or phosphonate (VIIB) wherein $R_u$ is $OR_v$ does not proceed directly to compound (II) but proceeds via a carboxylic ester which is then converted into the corresponding alcohol with a reducing agent, suitably a complex metal reducing agent such as lithium aluminium hydride (LiAlH$_4$), diisobutyl aluminium hydride (DIBAH) or lithium borohydride (LiBH$_4$), in any suitable aprotic solvent for example methylene dichloride, chloroform, dioxane, diethyl ether or THF, at any temperature providing a suitable rate of formation of the required product, such as a temperature in the range of from −30° C. to 60° C., for example at room temperature. Then, the intermediate alcohol is oxidised to aldehyde (II) with an oxidising agent such as manganese dioxide, periodinane (Dess-Martin reagent), pyridinium chlorochromate (PCC) or pyridinium dichromate (PDC) or a combination of oxalyl chloride and DMSO (Swern reaction), preferably manganese dioxide in methylene dichloride.

The compounds of formula (IIIA) are known, commercially available compounds or can be prepared from commercially available compounds. In particular, compounds (IIIA) in which X is $R_9N$, can be prepared by alkylation of compounds (IIIA) in which X is NH with halides of formula $R_9$Hal, in which Hal is a halogen atom, suitably bromo or iodo, and in the presence of a base such as sodium hydride, potassium t-butoxide, sodium methoxide and the like.

A compound of formula (IIIB) is prepared according to the reaction sequence shown in Scheme (II) below (Tetrahedron, 48, 3991–4004, 1992).

Scheme (II)

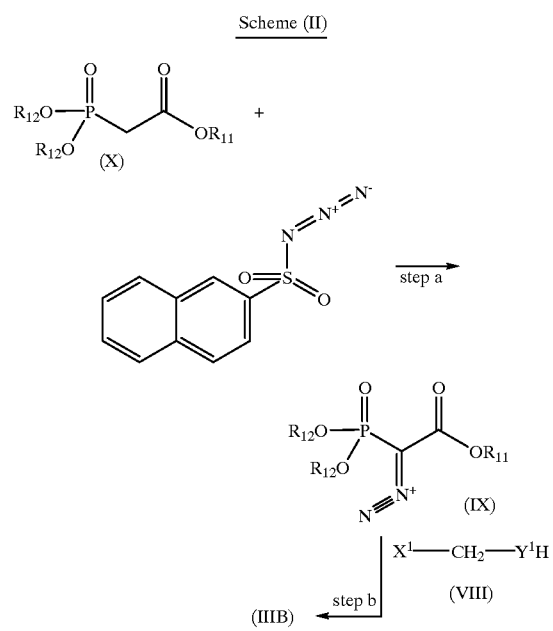

wherein, subject to any qualification mentioned below, $R_{11}$, $R_{12}$, $X_1$ and $Y_1$ are as defined in relation to formula (IIIB).

The reaction a) between 2-naphthalenesulphonyl azide and the compound of formula (X) is effected in an aromatic hydrocarbon solvent such as toluene, usually at temperatures in the range of from 0° C. to room temperature and in the presence of a base such as potassium tert-butoxide; preferably the reaction is carried out in an inert atmosphere.

The formation of compound (IIIB) from azide (IX) and compound (VIII) is suitably carried out in a solvent such as tetrahydrofuran, methylene dichloride or toluene, usually at an elevated temperature such as the reflux temperature of the solvent; preferably the reaction is carried out in the presence of a catalytic amount of rhodium tetraacetate.

The compounds of formula (IIIC) are known compounds or they are prepared according to procedures analogues to those used to prepare known compounds, for example, those methods disclosed in J. Med. Chem. 30 (1987) 1995.

A compound of formula (VI), wherein $R_4$ is other than hydrogen is prepared by condensing a compound of formula (XI):

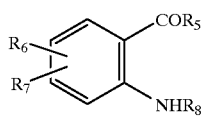 (XI)

wherein $R_5$, $R_6$, $R_7$ and $R_8$ are as defined in relation to formula (I), with a haloketone of formula (XII):

 (XII)

wherein $X_3$ is halo, especially bromo, and $R_{4a}$ is $R_4$ as defined in formula (VI) or a group which can be converted into $R_4$.

The reaction between the compounds of formula (XI) and (XII) is carried out using conventional condensation conditions, usually in an aprotic solvent such as DMF and preferably at an elevated temperature, for example in the range of from 80° C. to 90° C.: Such conditions are described in *J. Org. Chem.*, 37 (1972), 3622.

The compounds of formula (XI) and (XII) are known compounds or they are prepared using to methods analogous to those used to prepare known compounds, such as those disclosed in *J. Org. Chem.*, 37 (1972), 3622.

A compound of formula (V), that is a compound of formula (VI) wherein $R_4$ is hydrogen, is prepared according to the reaction sequence set out in Scheme (III):

ethanol, in the presence of a base such as potassium ethoxide (conveniently provided by adding metallic potassium to ethanol solvent), and usually at room temperature;

step b, reduction and cyclisation, is conveniently accomplished using iron powder in an ethanol/acetic acid solvent mixture, at an elevated temperature such as the reflux temperature of the solvent;

step c, is carried out using conventional alkylation conditions, for example in an aprotic solvent such as THF or DMF using a base such as sodium hydrideor in acetone using solid potassium hydroxide, preferably, sodium hydride in DMF, and usually at ambient temperature;

step d, the reduction step, may be carried out using any reducing agent, suitably a complex metal reducing agent such as lithium aluminium hydride (LiAlH$_4$), diisobutyl aluminium hydride (DIBAH) or lithium borohydride (LiBH$_4$), in any suitable aprotic solvent for example, hexane, dioxane, diethyl ether or THF, preferably under anhydrous conditions and preferably under an inert atmosphere such as argon at any temperature providing a suitable rate of formation of the required product, such as a temperature in the range of from −30° C. to 60° C., for example in the range of from −20° C. to 0° C.

step d, is carried out using an oxidising agent such as manganese dioxide, periodinane (Dess-Martin reagent), pyridinium chlorochromate (PCC) or pyridinium dichromate (PDC) or a combination of oxalyl chloride and DMSO (Swern reaction), preferably manganese dioxide in methylene dichloride, usually at ambient temperature.

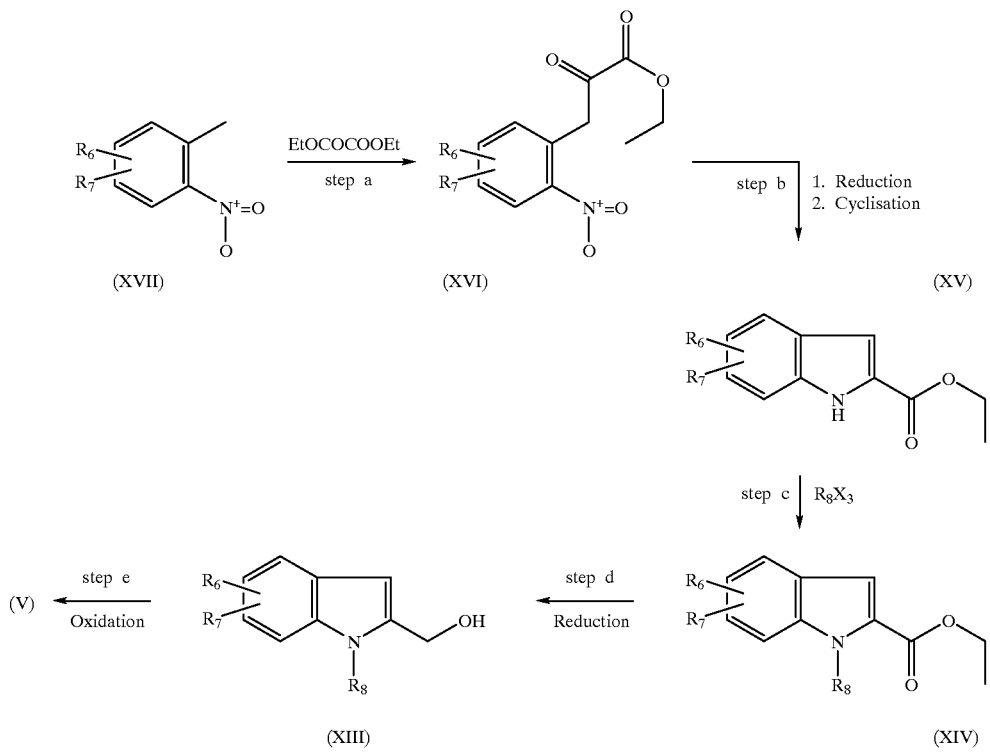

wherein, subject to any qualification mentioned below, $R_6$, $R_7$ and $R_8$ are as defined in relation to formula (I).

In Scheme (III)

step a, is suitably carried out in a solvent such as ethanol or solvent mixtures thereof, for example diethylether/

The compounds of formula (VIIA) and (VIIB), are known compounds or they are prepared using methods analogous to those used to prepare known compounds, such as those described in *Organic reactions*, Vol 14, 270–490, Wiley Interscience.

The compounds of formula (IV), (X) and (XVII) are known compounds or they are prepared using methods analogous to those used to prepare known compounds, such as those described in J. March, *Advanced Organic Chemistry*, 3rd Edition (1985), Wiley Interscience, *Organic Synthesis*, Coll. 5, 872–874 and *Organic Synthesis*, Coll. 5, 567–571.

The compounds of formula (VIII) can be prepared according to the methods known in the literature, for example in *Tetrahedron*, 48, 3991–4004, 1992. When necessary, compounds of formula (VIII) in which $X^1$ is a protected hydroxy group can be deprotected to free hydroxy groups by conventional methods and then optionally converted to compounds (VIII) in which $X^1$ is $R_9NH$ by methods known to those skilled in the art (e.g. via an intermediate mesyl derivative and subsequent reaction with $R_9NH_2$ or via the aldehyde, obtained by oxidation, and reductive amination with $R_9NH_2$ in the presence of sodium cyanoboro hydride.

Amines of general formula $HNR_sR_t$ may be prepared using the methods known in the art for the preparation of amines, for example as taught in *Houben-Weil, Methoden der Organischen Chemie*, Vol. XI/1 (1957) and Vol. E16d/2 (1992), Georg Thieme Verlag, Stuttgart.

In particular, amines of the general formula $HNR_sR_t$ wherein one of $R_s$ and $R_t$ represents hydrogen and the other represents a moiety (a), (b), (c), (d) (e) as defined above or a particular example thereof, are prepared according to the methods summarised in Scheme (V) below:

SCHEME (V)

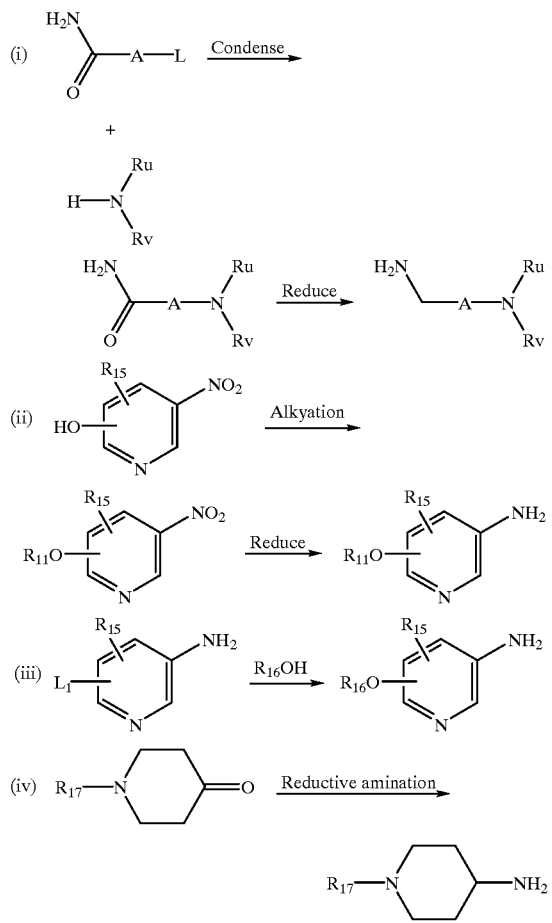

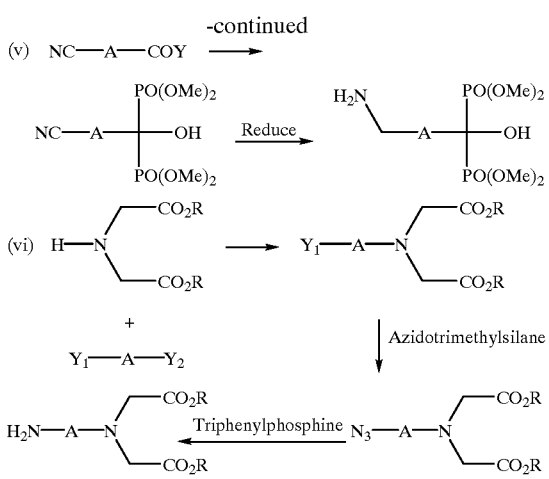

wherein R an alkyl or aryl group, $R_u$ and $R_v$ are as defined above, A is a bond or an alkyl chain, $R_{15}$ is hydrogen (in ii) or halogen (in (iii)) and $R_{16}$ is an alkyl group, $R_{17}$ is alkyl or aryl, L and $L_1$ are leaving groups, for example halogen or mesylate, Y is halogen, $Y_1$ is a leaving group, for example a halogen and $Y_1$ and $Y_2$ are leaving groups such as halogens, for example $Y_1$ is chloride and $Y_2$ is bromine.

With regard to Scheme (V):

The reduction of the amide function in (i) is suitably carried out using known methods, for example by using mixed hydride reducing agents, such as lithium aluminium hydride and methods described in *Org Synth* Coll Vol 4 564.

The reduction of the nitropyridine in (ii) is suitably carried out using the method described in *J. Org. Chem.* 58, 4742 (1993).

The alkylation of the hydroxy-nitropyridine in (ii) may be effected by using the method described in *J. Org. Chem* 55, 2964 (1990).

The displacement reaction in (iii) is suitably carried out using the method described in *Helvetica Chemica Acta* 47 (2), 45 (1964).

The reductive amination of the ketone in (iv) can be performed with benzylamine to give an imine intermediate which is then reduced using known methods and reducing agents such as sodium borohydride or lithium aluminium hydride. Debenzylation can then be performed again using conventional methods, for example with hydrogen in the presence of a catalyst such as palladium on charcoal.

The reduction of the nitrile in (v) is suitably carried by catalytic hydrogenation over platinium oxide.

The reaction of acid halide NC—A—COY to provide the dialkylphosphonate in (v) is effected by following the procedure described in *J Org Chem* 36, 3843 (1971).

The reaction of the azide with triphenylphosphine in (vi) is carried out in wet tetrahydrofuran as described in *Bull Soc Chim Fr* 1985, 815.

The azides in (vi) are prepared as shown using azidotrimethylsilane, following the procedure described in Synthesis 1995, 376.

The reaction of compound $Y_1$—A—$Y_2$ and the amine derivative in (vi) proceeds under conventional displacement reaction conditions.

The substrates in the above reactions (i), (ii), (iii), (iv), (v) and (vi) are known commercially available compounds.

A compound of formula (I) or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers and diastereoisomers by conventional means, for example by the use of an optically active acid as a resolving agent. Suitable optically active acids which may be used as resolving agents are described in "Topics in Stereochemistry", Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropriate silylating agent such as di-tert-butylsilylbis (trifluoromethanesulfonate): the silyl group may then be removed using conventional procedures such as treatment with hydrogen fluoride, preferably in the form of a pyridine complex and optionally in the presence of alumina, or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in ethyl acetate or trifluoroacetic acid in methylene dichloride. An amino group may be protected as a benzyl derivative, prepared from the appropriate amine and a benzyl halide under basic conditions, the benzyl group being removed by catalytic hydrogenolysis, using for example a palladium on carbon catalyst.

Indole NH groups and the like may be protected using any conventional group, for example benzenesulphonyl, methylsulphonyl, tosyl, formyl, acetyl (all of them removable by treatment with alkaline reagents), benzyl (removable either with sodium in liquid ammonia or with $AlCl_3$ in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl) ethoxymethyl (SEM) (removable by treatment with tetrabutylammonium fluoride in the presence of ethylenediamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The salts, esters, amides and solvates of the compounds mentioned herein may as required be produced by methods conventional in the art: for example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_sR_t$ may be prepared by treating the relevant carboxylic acid with an amine of formula $HNR_sR_t$ wherein $R_s$ and $R_t$ are as defined above. Alternatively, a $C_{1-6}$ alkyl ester such as a methyl ester of the acid may be treated with an amine of the above defined formula $HNR_sR_t$ to provide the required amide.

As mentioned above the compounds of the invention are indicated as having useful therapeutic properties:

The present invention therefore provides a method for the treatment and/or prophylaxis of diseases associated with over activity of osteoclasts in mammals which method comprises the administration of an effective non-toxic amount of a selective inhibitor of mammalian osteoclasts.

A suitable selective inhibitor of a mammalian osteoclast is a selective inhibitor of the vacuolar ATPase located on the ruffled border of mammalian osteoclasts.

One particular selective inhibitor of mammalian vacuolar ATPase is a compound of formula (I), or a pharmaceutically acceptable salt thereof, or a pharmaceutically acceptable solvate thereof.

Thus, the present invention further provides a method for the treatment of osteoporosis and related osteopenic diseases in a human or non-human mammal, which comprises administering an effective, non-toxic, amount of a compound of formula (I) or a pharmaceutically acceptable solvate thereof, to a human or non-human mammal in need thereof.

In a further aspect, the present invention provides an inhibitor of a mammalian osteoclasts, for example a compound of formula (I) or a pharmaceutically acceptable salt thereof, or a pharmaceutically acceptable solvate thereof, for use as an active therapeutic substance.

In particular the present invention provides a compound of formula (I) or a pharmaceutically acceptable salt thereof and/or a pharmaceutically acceptable solvate thereof, for use in the treatment of and/or prophylaxis of osteoporosis and related osteopenic diseases.

Of particular interest is the osteoporosis associated with the peri and post menopausal conditions. Also encompassed are the treatment and prophylaxis of Paget's disease, hypercalcemia associated with bone neoplasms and all the types of osteoporotic diseases as classified below according to their etiology:

Primary Osteoporosis
  Involutional
  Type I or postmenopausal
  Type II or senile
  Juvenile
  Idiopathic in young adults
Secondary Osteoporosis
  Endocrine abnormality
  Hyperthyroidism
  Hypogonadism
  Ovarian agenesis or Turner's syndrome Hyperadrenocorticism or Cushing's syndrome
Hyperparathyroidism
Bone marrow abnormalities
Multiple myeloma and related disorders
Systemic mastocytosis
Disseminated carcinoma
Gaucher's disease
Connective tissue abnormalities
Osteogenesis imperfecta
Homocystinuria
Ehlers-Danlos syndrome
Marfan's syndrome
Menke's syndrome
Miscellaneous causes
Immobilisation or weightlessness
Sudeck's atrophy
Chronic obstructive pulmonary disease
Chronic alcoholism
Chronic heparin administration
Chronic ingestion of anticonvulsant drugs In addition the invention encompasses the treatment of tumours, especially those related to renal cancer, melanoma, colon cancer, lung cancer and leukemia, viral conditions (for example those involving Semliki Forest virus, Vesicular Stomatitis virus, Newcastle Disease virus, Influenza A and B viruses, HIV virus), ulcers (for example chronic gastritis and peptic ulcer induced by *Helicobacter pylori*), for use as immunosupressant agents in autoimmune diseases and transplantation, antilipidemic agents for the treatment and/or prevention of hypercholesterolemic and atherosclerotic diseases and to be useful for the treatment of AIDS and Alzheimer's disease. These compounds are also considered useful in treating angiogenic diseases, i.e. those pathological conditions which are dependent on angiogenesis, such as rheumatoid arthritis, diabetic retinopathy, psoriasis and solid tumours.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a selective inhibitor of the pharmacological activity of human osteoclast cells, in particular the bone resorption activity of human osteoclast cells associated with abnormal loss of bone mass, and a pharmaceutically acceptable carrier thereof.

A particular inhibitor of human osteoclast cells is a selective inhibitor of human osteoclast vacuolar ATPase such as a compound of formula (I), or a pharmaceutically acceptable salt thereof, or a pharmaceutically acceptable solvate thereof, and a pharmaceutically acceptable carrier thereof.

Active compounds or a pharmaceutically acceptable salt thereof and/or a pharmaceutically acceptable solvate thereof is normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated an the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily dose is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

At the above described dosage range, no toxicological effects are indicated for the compounds of the invention.

The present invention also provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal, which comprises administering an effective, non-toxic, amount of a compound of formula (I) or a pharmaceutically acceptable solvate thereof, to a human or non-human mammal in need thereof.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

The present invention also provides the use of a selective inhibitor of the biological activity of human osteoclast cells, in particular the bone resorption activity of human osteoclast cells associated with abnormal loss of bone mass, compound of formula (I), or a pharmaceutically acceptable salt thereof, or a pharmaceutically acceptable solvate thereof, for the manufacture of a medicament for the treatment and/or prophylaxis of diseases associated with over activity of osteoclasts in mammals, such as the treatment and/or prophylaxis of osteoporosis and related osteopenic diseases.

The present invention also provides the use of a selective inhibitor of the biological activity of human osteoclast cells, in particular the bone resorption activity of human osteoclast cells associated with abnormal loss of bone mass, for the manufacture of a medicament for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

Preparation 1
2-Naphthalenesulfonyl azide

A solution of sodium azide (3.1 g, 44 mmol) in water (10 ml) was added dropwise at RT to a stirred solution of 2-naphthalenesulfonyl chloride (10 g, 44 mmol) in acetone (60 ml) and stirring was continued for 2 hours. Water (50 ml) was added and the resulting mixture was decanted. The surnatant was discarded, while the brown oily residue was recrystallized from light petroleum producing after drying pure title compound (7.67 g, 32.9 mmol, yield 74.7%) as white needles, m.p.=45°.

Preparation 2
Ethyl diazo(diethoxyphosphoryl)acetate

A suspension of potassium t-butoxide (4.42 g, 39.4 mmol) in toluene (200 ml) was stirred at 0° under Ar for 10 minutes. A solution of ethyl diethoxyphosphoryl acetate (6.53 ml, 32.9 mmol) in toluene (20 ml) was added in 20 minutes keeping the temperature below 5°. Another solution of 2-naphthalenesulfonyl azide (7.67 g, 32.9 mmol) was added dropwise below 5°, and the reaction mixture was warmed to RT and stirred overnight. The resulting suspension was filtered and the filtrate washed with toluene. The pooled organic phase was concentrated and the brown oily residue distilled producing pure title compound (6.12 g, 24.5 mmol, yield 74.3%) as a yellow oil, b.p.=70–73°/0.02 mmHg.

Preparation 3
Ethyl [(2-ethencarbonyloxy)ethoxy]diethoxyphosphoryl acetate

A solution of ethyl diazo(diethoxyphosphoryl)acetate (1.01 g, 4.0 mmoles), ethanediol monoacrylate (0.465 ml, 4 mmol) and rhodium (II) acetate dimer (34 mg, 0.080 mmol) in toluene (20 ml) was refluxed for 3 hours. After cooling to RT and filtering the mixture through a Celite pad, the solvent was concentrated and the residue was pure title compound (960 mg, 2.84 mmol, yield 70.9%) as a green oil.

EXAMPLE 1

(2Z,4E) 3-[3-(5,6-Dichloro-1H-indol-2-yl)-2-propenyliden]-1,4-dioxan-2-one

A solution of ethyl[(2-ethencarbonyloxy)ethoxy] diethoxyphosphoryl acetate (1.00 g, 2.96 mmol) and tetramethylguanidine (0.371 mL, 2.96 mmol) in toluene (20 ml) was stirred for 10 minutes at RT. Then (2E) 3-(5,6-dichloro-1H-indol-2-yl)-prop-2-enal (710 mg, 2.65 mmol) was added and the mixture was heated at 100° (bath temperature) overnight. After cooling at RT the solvent was concentrated and the residue dissolved in EtOAc, washed with 1N HCl and brine, then dried (MgSO$_4$) and concentrated to give an oily residue. This was chromatographed on silicagel (n-heptane/EtOAc 2/1). The collected fractions were pooled and concentrated to give pure title compound (85% purity as judged by $^1$H NMR, 70 mg, 0.184 mmol, yield 6.9%) as yellow crystals, m.p.=208–210°.

$^1$H NMR (DMSO-d$_6$): 11.80 (s, 1H); 7.76 (s, 1H); 7.56 (s, 1H); 7.16 (dd, 1H); 6.95 (d, 1H); 6.68 (d, 1H), 6.60 (s, 1H); 4.57 (m, 2H); 4.31 (m, 2H).

Preparation 4
Ethyl α-oxo-3-(2-nitro-4,5-dichlorophenyl)propanoate

To a suspension of potassium (24.5 g, 0.626 g.a.) in anhydrous Et$_2$O (245 ml), a solution of absolute EtOH (158 ml) and anhydrous Et$_2$O (126 ml) was added dropwise under nitrogen during four hours. The resulting solution was diluted with Et$_2$O (600 ml) and then diethyl oxalate (85.5 ml, 630 mmol) was added dropwise in about 30 min. To the resulting yellow mixture, a solution of 3-nitro-4,5-dichlorotoluene (130 g, 630 mmol) in anhydrous $Et_2O$ (225 ml) was added dropwise in 1 hour at RT. Stirring was continued for additional three hours and the dark-brown mixture was settled at RT for two days. The potassium salt was collected by filtration, washed with $Et_2O$ (200 ml) and dried to give 210 g of a dark-brown powder. The solid was suspended in a mixture of water (200 ml) and EtOAc (400 ml) and then acidified with 10% HCl. The organic layer was washed with brine, dried over $Na_2SO_4$ and evaporated under vacuum to obtain pure title compound (115.1 g, 375.8 mmol, yield 59.7%) as a light brown solid, m.p.=92–94° C.

Preparation 5
Ethyl 5,6-dichloro-1H-indole-2-carboxylate

A mixture of ethyl α-oxo-3-(2-nitro-4,5-dichlorophenyl) propanoate (100 g, 327 mmol) and iron powder (160 g) in EtOH (625 ml) and acetic acid (625 ml) was refluxed for two hours. After cooling, the resulting mixture was evaporated under vacuum and the solid residue was dissolved in THF (1000 ml) and chromatographed on Florisil (500 g) eluting with THF (5000 ml). Evaporation of the collected fractions gave pure title compound (77.5 g, 301 mmol, yield 92.0%) as a light brown powder, m.p. 215°–218° C.

Preparation 6
5,6-Dichloro-1H-indole-2-carboxaldehyde

Ethyl 5,6-dichloro-1H-indole-2-carboxylate (77.5 g, 301 mmol) dissolved in dry THF (70 ml) was added dropwise to an ice cold solution of $LiAlH_4$ (19.17 g, 505 mmol) in anhydrous THF (1000 ml) under nitrogen. The mixture was stirred for 45 min at 0° C. and then quenched by the sequential addition of water (20 ml), 15% aqueous NaOH (20 ml) and water (60 ml). The mixture was filtered through-a Celite pad and then washed with THF (2×500 ml). The filtrate dried over $Na_2SO_4$ and evaporated at reduced pressure yielded an orange raw solid. This was dissolved in $CH_2Cl_2$ (1500 ml) and activated $MnO_2$ (150 g, 1.73 mol) was added. The mixture was stirred at RT for 12 hours and then filtered through a Celite pad which was washed with warm acetone (4×750 ml), and the combined filtrates were evaporated to dryness, yielding pure title compound (42.1 g, 197 mmol, yield 65.4%), mp=207–208° C.

Preparation 7
(E) Ethyl 3-(5,6-dichloro-1H-indol-2-yl)-2-propenoate 5,6-Dichloro-1H-indole-2-carboxaldehyde (35 g, 164 mmol) and (ethoxycarbonylmethylene) triphenylphosphorane (60 g, 176 mmol) were dissolved in toluene and refluxed for three hours. The solvent was evaporated under reduced pressure and the reaction mixture was purified by chromatography on silicagel (n-hexane/AcOEt, 8/2) obtaining pure title compound (28 g, 98.5 mmol, yield 60.1%).

Preparation 8
(E) 3-(5,6-Dichloro-1H-2-indol-2-yl)-2-propen-1-ol (E) ethyl 3-(5,6-dichloro-2indolyl)-2-propenoate (16.23 g, 57.1 mmol) was dissolved under nitrogen in dry THF (300 ml) cooled at −20° and 1M DIBAL in hexanes (115 ml, 115 ml) was added dropwise at −20° C. The reaction mixture was maintained at this temperature for 1 hour and then quenched with $H_2O$. The mixture was warmed to RT, diluted with $Et_2O$ (200 ml) and filtered on a Celite pad, washing with 300 ml of $Et_2O$. The dark-red solution was dried over $MgSO_4$ and evaporated under vacuum to give pure title compound (13.8 g, 57.0 mmol, yield 99.8%).

Preparation 9
(E) 3-(5,6-Dichloro-1H-indol-2-yl)-2-propenaldehyde

To a solution of (E) 3-(5,6-dichloro-2-indolyl)-2-propen-1-ol (13.8 g, 57.0 mmol) in $Et_2O$ (450 ml), activated $MnO_2$ (35 g) and NaCl (35 g) were added. The reaction mixture was stirred for two days at RT, filtered on a Celite pad, washed with $Et_2O$ and dried over $MgSO_4$ to afford (11.5 g, 47.9 mmol, yield 84.1%) of pure title compound.

Preparation 10
(±)3-bromo-1-methyl-2-pyrrolidone

A solution of (±)2,4-dibromobutanoyl chloride (10.6 g, 40 mmol) (J. Med. Chem., 1987, 30, 1197) in $CHCl_3$ (10 ml) was added dropwise under stirring at 0° to a 40% aqueous solution of $MeNH_2$ (8 ml, 80 mmol). After additional stirring for 30 minutes, a solution of NaOH (2.25 g, 56 mmol) in water (5.6 ml) was added keeping the temperature below 10°. After warming to RT and stirring for 1 hour, the water phase was decanted off and the organic phase was washed with 5% aqueous HCl and brine. After drying ($MgSO_4$) and evaporation of the solvent a yellow oily residue was obtained. This was dissolved in toluene (100 ml), cooled under stirring at 0° and 60% NaH (1.8 g) was added portionwise. Stirring was continued for 90 minutes, then the solution was poured into ice cold water (100 ml). The aqueous phase was saturated with NaCl and then extracted with $Et_2O$; the ethereal phase, after drying ($MgSO_4$) and concentrating, gave pure title compound (1.40 g, 7.86 mmol, yield 19.7%).

Preparation 11
(±)(1-methyl-2-pyrrolidon-3-yl)triphenylphosphonium bromide

A solution of (±)3-bromo-1-methyl-2-pyrrolidone (1.40 g, 7.86 mmol) and triphenylphosphine (2 g, 7.62 mmol) in THF (50 ml) was refluxed for 2 days. After cooling to RT the white solid formed was filtered, washed thoroughly with THF and dried to give pure title compound (900 mg, 2.04 mmol, yield 26.8%).

EXAMPLE 2

(2Z,4E)-5-(3-(5,6-dichloro-1H-indol-2-yl)-2-propenylidene)-1-methyl-2-pyrrolidone A suspension of (E) 3-(5,6-dichloro-1H-indol-2-yl)-2-propenaldehyde (240 mg, 1 mmol), (±)(1-methyl-2-pyrrolidon-3-yl)triphenylphosphonium bromide (500 mg, 1.11 mmol) and triethylamine (0.35 ml, 2.50 mmol) in EtOH (10 ml) was heated at 60° under stirring for 2 hours. After cooling to RT the yellow solid formed was filtered and washed repeatedly with EtOH. After drying pure title compound was obtained (250 mg, 0.778 mmol, yield 77.8%) as yellow cristals, m.p.=304° dec.

$^1$H-NMR (DMSO-$d_6$): 11.72 (bs, 1H); 7.76 (s, 1H); 7.54 (s, 1H); 6.80–7.13 (m, 3H); 6.61 (s, 1H); 3.46 (t, 2H); 2.86 (bs, 5H).

EXAMPLE 3

(2Z,4E)-5-(3-(5,6-Dichloro-1H-indol-2-yl)-2-propenylidene)-3-methyl-2-thioxothiazolidin-4-one A solution of (E) 3-(5,6-dichloro-1H-indol-2-yl)-2-propenaldehyde (870 mg, 3.62 mmol), N-methylrhodanine (555 mg, 3.77 mmol) and sodium acetate (1.03 g) in glacial acetic acid (18 ml) was refluxed under Ar for 17 hours. After cooling to RT and evaporation of the solvent the residue was taken up with water (20 ml) and extracted with $CH_2Cl_2$ (2×20 ml). The organic phase gave after drying ($MgSO_4$) and concentrating a brown residue (600 mg) that was chromatographed on silicagel (n-heptane/AcOEt 4/1). The pooled fractions produced a better residue that was again chromatographed on silicagel ($CH_2Cl_2$). The pooled fractions were triturated with $Et_2O$ to give a residue (36 mg) after filtration. This was triturated with acetonitrile to give finally after drying pure title compound (28 mg, 0.076 mmol, yield 2.1%) as brown crystals, m.p.=283°.

$^1$H-NMR (DMSO-$d_6$): 11.89 (bs, 1H); 7.84 (s, 1H); 7.60 (s, 1H); 7.57 (d, 1H); 7.39 (d, 1H); 7.02 (dd, 1H); 6.84 (s, 1H); 3.37 (s, 3 2H).

| LIST OF ABBREVIATIONS USED IN THE ABOVE PREPARATIONS AND EXAMPLES | |
|---|---|
| Celite | Registered trade mark for dicalite |
| DMF | Dimethylformamide |
| EI | Electron Impact |
| AcOEt | Ethyl acetate |
| FAB POS | Fast Atom Bombardment/Positive ions detection |
| MS | Mass Spectrum |
| THF | Tetrahydrofuran |
| TSP | ThermoSpray |

Biological Assays

Background. It is known that, upon attachment to bone, an electrogenic H$^+$-adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., Science, 245, 855 (1989)] and than confirmed by Bekker [P. J. Bekker et al., J. Bone Min. Res., 5, 569 (1990)] and Väänänen [K. K. Väänänen et al., J. Cell. Biol., 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin $A_1$, a selective inhibitor of vacuolar H$^+$-ATPases [J. E. Bowman et al., Proc. Natl. Acad. Sci. USA, 85, 7972 (1988)], whilst it was not inhibited by ouabain, an inhibitor of Na$^+$/K$^+$-ATPases; sodium orthovanadate, an inhibitor of p-ATPases, or by omeprazole or SCH 28080, both of which are inhibitors of gastric H$^+$/K$^+$-ATPase [J. P. Mattson et al., Acta Physiol. Scand., 146, 253 (1992)].

It is known that specific inhibitors of vacuolar ATPases, such as bafilomycin $A_1$, are able to inhibit bone resorption in osteoclast cultures [K. Sundquist et al., Biochem. Biophys. Res. Commun. 168, 309–313 (1990)].

Inhibition of Proton Transport and v-ATPase Activity in Membrane Vesicles

Preparation of crude bone microsomes from calcium-starved egg-laying hens. Vesicles were prepared from medullar bone obtained from tibiae and femurs of egg-laying hens which were calcium-starved for at least 15 days. Briefly, bone fragments were scraped with a 24 scalpel blade, suspended in 40 ml of isolation medium (0.2 M sucrose, 50 mM KCl, 10 mM Hepes, 1 mM EGTA, 2 mM dithiotheitrol, pH 7.4) and filtered through a 100 µm pore size nylon mesh. The whole procedure was performed at 4° C. After homogenisation in a potter (20 strokes) in 40 ml of isolation medium an initial centrifugation (6,500×$g_{max}$×20 min) was performed to remove mitochondria and lysosomes. The supernatant was centrifuged at 100,000×$g_{max}$ for 1 hr and the pellet was collected in 1 ml of isolation medium, divided into 200 µl aliquots, immediately frozen in liquid nitrogen and stored at −80° C. The protein content was determined using a Biorad colourimetric kit according to Bradford [M. Bradford, Ana. Biochem., 72, 248 (1976)]. For the proton transport assay, 5–10 µl of membranes were used.

Purification of osteoclast membranes. 1 ml of crude microsomal vesicles prepared above were applied (about 0.2 ml per tube ) on the top of a sucrose step-gradient consisting of 3.5 ml of 15%, 30% and 45% (w/w) sucrose in isolation medium and centrifuged at 280,000 $g_{max}$ for 2 hours (SW 41 Ti rotor). After centrifugation the 30–45% sucrose interfaces were collected, diluted approx. 20-fold in isolation medium and pelletted at 100,000 $g_{max}$ for 1 hour (SW 28 rotor). The pellet was then resuspended in 1 ml of isolation medium, aliquoted and frozen in liquid $N_2$ and stored at −80° C. until used.

Proton transport in membrane vesicles was assessed, semi-quantitatively, by measuring the initial slope of fluorescence quench of acridine orange (excitation 490 nm; emission 530) after addition of 5–20 µl of membrane vesicles in 1 ml of buffer containing 0.2 M sucrose, 50 mM KCl, 10 mM Hepes pH 7.4, 1 mM ATP.Na$_2$, 1 mM CDTA, 5 µM valinomycin and 4 µM acridine orange. The reaction was started by addition of 5 mM MgSO$_4$. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin Al. The reaction medium contained 1 mM ATP, 10 mM HEPES-Tris pH 8, 50 mM KCl, 5 uM valinomycin, 5 uM nigericin, 1 mM CDTA-Tris, 100 uM ammonium molybdate, 0.2 M sucrose and membranes (20 ug protein/ml). The reaction was initiated by MgSO$_4$ (8-arm pipette) and stopped, after 30 min, by addition of 4 volumes of the malachite green reagent (96-arm pipette) prepared according to Chan [Anal. Biochem. 157, 375 (1986)]. Absorbance at 650 nm was measured after 2 min using a microplate reader. Results are expressed as µmol (Pi)×mg protein$^{-1}$×hour$^{-1}$ and, for each experiment, represent the mean±sem of triplicates.

Pharmacological Data

Inhibition of Bafilomycin-Sensitive ATPase in Chicken Osteoclasts

| Ex. No | IC$_{50}$ (µM) APase assay |
|---|---|
| 1 | 8.5 |

Inhibition of Bone Resorption
In Vitro Assays

1) Bone resorption by disaggregated rat osteoclasts can be assessed as described previously in the literature [T. J. Chambers et al., Endocrinology, 1985, 116, 234]. Briefly, osteoclasts were mechanically disaggregated from neonatal rat long bones into Hepes-buffered medium 199 (Flow, UK). The suspension was agitated with a pipette, and the larger fragments were allowed to settle for 30 sec. The cells were then added to two wells of a multiwell dish containing bone slices (each measuring 12 mm$^2$). After 15 min at 37° C. the bone slices were removed, washed in medium 199 and placed in individual wells of a 96-well plate. These were incubated for 24 hrs in a total volume of 2 ml of culture medium, consisting of 10% foetal calf serum in Hanks-buffered MEM, in the presence or absence of drug. The number of osteoclasts and bone resorption were quantified by confocal laser scanning microscopy (CLSM): the bone slices were fixed with 2% glutaraldehyde in 0.2 M cacodylate buffer and the osteoclasts on each bone slice were stained for tartrate-resistant acid phosphatase. After counting the number of large, multinucleated, red-stained cells, the bone slices were immersed in 10% sodium hypochlorite for 5 min to remove cells washed in distilled water and sputter-coated with gold. The entire surface of each bone slice was then examined in CLSM. The number and the size of the osteoclastic excavations, the plain area and the volume of bone resorbed was recorded. Results were expressed as mean pit number per bone slice, mean pit number per osteoclast, mean area per osteoclast or mean volume per osteoclast.

2) Bone resorption by human osteoclasts can be assessed using a modification of the method above. Briefly, human osteoclasts are purified from human giant cell tumours by negative selection using Pan Human HLA II antibodies in conjunction with Dynal magnetic beads. Osteoclasts are seeded onto bovine bone slices in Hepes-buffered medium 199 (Flow, UK). After 30 minutes, the bone slices are transferred into a 24-well multi-plate (4 slices per well) containing 2 ml/well of medium, consisting of 10% foetal calf serum in D-MEM. One hour later, vehicle (DMSO) or test compounds at different concentrations in DMSO were added and incubation was continued for 47 hours. Bone slices were then treated and analysed as described above for the rat osteoclast assay.

3) Inhibition of PTH-stimulated $^{45}Ca^{2+}$ release from pre-labelled foetal rat long bone. The assay is based on that described by Raisz (*J. Clin. Invest.* 44:103–116, 1965). Time-mated Sprague-Dawley rats were injected subcutaneously with 200 mCi of $^{45}CaCl2$ on the 18th day of gestation. On the following day, the foetuses were removed aseptically and the radii and ulnae were dissected free of adjacent soft tissue and the cartilaginous ends, and then cultured for 24 hr at 37° C. in BGJ medium containing 1 mg/ml BSA. The bones were then transferred to fresh medium containing the test compounds (0.1–50 μM) with and without PTH (12 nM) and were incubated for an additional 48 hr. The media were collected and the bones extracted to determine the mean % calcium release by scintillation counting. Results were expressed as the % inhibition compared to the amount of calcium released from cultures incubated with PTH alone.

In Vitro Assays

Prevention of retinoid-induced hypercalcaemia. The method used was that described by Trechsel et al., (*J. Clin. Invest.* 80:1679–1686, 1987). Briefly, male Sprague-Dawley rats weighing 160–200 g (10 per group) were thyroparathyroidectomised and were treated subcutaneously with the retinoid Ro 13-6298 (30 μg/day) for three days and this was found to significantly increase blood serum calcium by 4–5 mg/100 ml. For inhibition of this effect, rats were treated simultaneously with test compounds i.v. or p.o. at 0.1–100 mg/kg, or vehicle and blood calcium was measured as described above, before treatment and one day after the last administration. Results were expressed as % inhibition with respect to vehicle-treated animals.

Prevention of bone loss in osteoporosis induced by ovariectomy and immobilisation. Seven groups of 10 Sprague-Dawley rats (200 g) underwent ovariectomy plus neurectomy of the sciatic nerve in the right hind limb, while one group was sham-operated according to the method described by Hayashi et al., (*Bone* 10:25–28, 1989). It was demonstrated that a steady-state was attained in the amount of trabecular bone lost 6–12 weeks after the operations. During a 6-week period, the operated animals received the test compounds (0.1–100 mg/kg p.o. u.i.d.), or vehicle. At the end of this treatment period, the animals were sacrificed and the tibia and femur of the hind limb removed. The tibia wet and dry weight were determined, and the density (displacement of water) and ashes content (total weight, calcium and phosphorous content) also measured. The femur were fixed in 10% formalin, de-mineralised in 5% formic acid and the coronal midshaft and longitudinal section of the distal metaphysis cut and stained with haematoxilin and eosin. Histomorphometric evaluation was made using a semi-automated image analyser (Immagini & Computer, Milan, Italy). In the distal metaphysis, the % trabecular bone area in the secondary spongiosa (which is the trabecular bone 1 mm from the epiphyseal growth plate to about 4 mm towards the midshaft giving a total area of 5 mm$^2$) and the number of trabeculae (according to Parfitt et al., *J. Bone Min. Res.* 2: 595, (1987)) were determined in all animals. In the midshaft, the medullary, cortical (CA) and total (TA) cross-sectional area was measured and the cortical index (CI) determined from the formula CI=CA/TA.

Prevention of bone loss in ovariectomised mature rats. The methodology employed is based on that described by Wronsky et al. [*J. Bone Min.Res.*, 6, 387 (1991)]. The bone loss, prevalently cancellous, occuring after the surgery is monitored by dual emission X-ray absorptiometry (DEXA) measurements of bone mineral density (BMD) of long bones and by HPLC measurements of urinary levels of products of bone collagen breakdown, such as the cross-link residues pyridinoline (PYD), deoxypyridinioline (DPD) and lysine glycosides, i.e. galactosyl-hydroxylysine (GHYL) and glucosyl-galactosyl-hydroxylysine (GGHYL).

Groups of 7–10 female Sprague-Dawley rats, about 90 days old and weighing 200–250 g are used. Rats are anesthetised by sodium pentobarbital (35 mg/kg i.v.), laparotomy is performed and ovaries are bilaterally removed. Wounds are adequately disinfected and sutured. A group is sham operated. During a 4-week experimental period, the operated animals receive test compounds in the appropriate vehicle (0.1–100 mg/kg p.o. u.i.d.) or vehicle alone.

Twenty-four-hr urine samples are collected for PYD, DPD, GHYL and GGHYL determinations before and 2, 4, 8, 11, 15, 18, 22 and 25 days after surgery. The aliquots of urine are frozen and stored at −20° C. until HPLC analysis.

Before and at the end of the experimental period, the bone metaphyseal mineral densities of left distal femur and proximal tibia were evaluated in vivo using lightly anaesthetised animals. Results are expressed as % of prevention versus vehicle treated animals.

Other Therapeutic Utilities

The activity of the compounds of the invention for the other utilities mentioned herein may be determined by according to the following methods which are incorporated herein:

1. Antitumor activity may be determined according to the methods disclosed in published International Application, Publication number 93/18652; in particular the screen employed, experimental details and bibliography of M. R. Boyd et al., *Status of the NCI preclinical antitumor drug discovery screen; principles and practices of Oncology*, 3, issue 10, October 1989, Lippincott.

2. Antiviral activity may be assessed using the in vitro assays reported by H. Ochiai et al., *Antiviral Research*, 27, 425–430 (1995) or by C. Serra et al., *Pharmacol. Res.*, 29, 359 (1994). Anti-HIV activity can be assessed as reported in the literature, for example by S. Velásquez et al., *J. Med. Chem.*, 38, 1641–1649 (1995).

3. Antiulcer activity may be assessed in vivo using the methods reported in the literature, for example, as described by C. J. Pfeiffer, *Peptic Ulcer*, C. J. Pfeiffer Ed., Munksgaard Publ., Copenhagen, 1971. In vitro assays for inhibition of vacuolization induced by *Helicobacter pylori* are described, for example, by E. Papini et al., *FEMS Microbiol. Lett.*, 113, 155–160 (1993).

4. Usefulness in treating Alzheimer's disease may be determined using models in vitro such as inhibition of amiloyd-β production as described in the literature by J. Knops et al., *J. Biol. Chem.*, 270, 2419–2422 (1995) or by models in vivo: such as the transgenic mouse model overexpressing human APP reported by D. Games et al., *Nature*, 373, 523–527 (1995).

5. Immunosuppressant activity can be assessed as reported in the literature, for example by M.-K. Hu et al., *J. Med. Chem.*, 38, 4164–4170 (1995).

6. Antilipidemic activity can be assessed as reported in the literature, for example by E. A. L. Biessen et al. *J. Med. Chem.*, 38, 1846–1852 (1995). Antiatherosclerotic activity may be assessed by using animal models of atherosclerosis, such as the atherosclerotic rabbit model, which are reported in the literature, for example by R. J. Lee et al., *J. Pharm. Exp. Ther.*, 184, 105–112 (1973).

7. Angiostatic activity may be assessed using the methods reported in the literature, for example as described by T. Ishii et al., *J. Antibiot.*, 48, 12 (1995).

We claim:

1. A compound of formula (I):

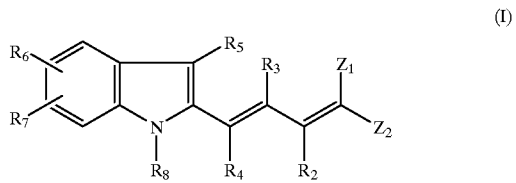

(I)

or a salt thereof, or a solvate thereof, wherein:

$R_2$, $R_3$ and $R_4$ each independently represent hydrogen, alkyl, aryl or substituted aryl;

$R_5$ represents hydrogen, alkyl, aryl or substituted aryl;

$R_6$ and $R_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino;

$R_8$ represents hydrogen, hydroxy, alkanoyl, alkyl, aminoalkyl, hydroxyalkyl, carboxyalkyl, carbalkoxyalkyl, carbamoyl or aminosulphonyl; and $Z_1$ and $Z_2$ together with the carbon atom to which they are attached represent a heterocyclic group.

2. A compound according to claim 1, wherein $Z_1$ and $Z_2$ together with the carbon atom to which they are attached represent a moiety of formula (a):

(a)

wherein the asterisked (*) carbon is attached to the double bond, $R_1$ represents hydrogen or a thioxo group, X represents O or $NR_9$ wherein $R_9$ is $C_{1-6}$ alkyl or an optionally substituted heterocyclic group or a group —T—$NR_sR_t$ wherein T is a $C_{1-6}$ alkylene group and $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together form a heterocyclic group; and Y represents $CH_2$, —$NR_{10}CH_2$— wherein $R_{10}$ is hydrogen or a $C_{1-6}$ alkyl group, or Y is —$OCH_2$— or S.

3. A compound according to claim 2, wherein the moiety of formula (a) is 1,4-dioxan-2-one, 1-methyl-2-pyrrolidone or 3-methyl-2-thioxothiazolidin-4-one.

4. A compound according to claim 1, wherein $R_2$, $R_3$ and $R_4$ each independently represents hydrogen, alkyl or phenyl.

5. A compound according to claim 1, wherein $R_6$ and $R_7$ each independently represents a halo group.

6. A process for preparing a compound of formula (I) or a salt thereof or a solvate thereof, which process comprises reacting a compound of formula (II):

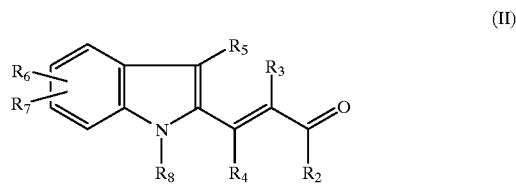

(II)

wherein $R_2$, $R_3$, $R_4$, $R_5$, $R_6$, $R_7$ and $R_8$ are as defined in relation to formula (I), with a reagent capable of converting a moiety of formula —$COR_2$ into a moiety of formula (b):

(b)

wherein $Z_1$ and $Z_2$ are as defined in relation to the compound of formula (I); and thereafter, as required carrying out one or more of the following reactions:

(i) converting one compound of formula (I) into another compound of formula (I);

(ii) removing any protecting group;

(iii) preparing a salt or a solvate of the compound so formed.

7. A pharmaceutical composition comprising a compound of formula (I) as defined in claim 1, or a pharmaceutically acceptable salt thereof or a pharmaceutically acceptable solvate thereof, and a pharmaceutically acceptable carrier therefor.

8. A method for the treatment and/or prophylaxis of diseases associated with over activity of osteoclasts in mammals which method comprises the administration of an effective non-toxic amount of a selective inhibitor of mammalian osteoclasts.

* * * * *